(12) United States Patent
Ineson

(10) Patent No.: US 10,631,923 B2
(45) Date of Patent: Apr. 28, 2020

(54) ADJUSTABLE ELECTROSURGICAL PENCIL

(71) Applicant: INSTRUVENTIONAL INC., Brampton (CA)

(72) Inventor: Leonard Ineson, Mississauga (CA)

(73) Assignee: COVIDIEN LP, Mansfield, MA (US)

( * ) Notice: Subject to any disclaimer, the term of this patent is extended or adjusted under 35 U.S.C. 154(b) by 947 days.

(21) Appl. No.: 15/023,489

(22) PCT Filed: Sep. 15, 2014

(86) PCT No.: PCT/CA2014/050876
§ 371 (c)(1),
(2) Date: Mar. 21, 2016

(87) PCT Pub. No.: WO2015/039232
PCT Pub. Date: Mar. 26, 2015

(65) Prior Publication Data
US 2016/0213422 A1 Jul. 28, 2016

(30) Foreign Application Priority Data

Sep. 20, 2013 (CA) .................................... 2827695

(51) Int. Cl.
*A61B 18/14* (2006.01)
*A61B 18/00* (2006.01)
*A61B 17/00* (2006.01)

(52) U.S. Cl.
CPC ...... *A61B 18/1477* (2013.01); *A61B 18/1402* (2013.01); *A61B 2017/00526* (2013.01);
(Continued)

(58) Field of Classification Search
CPC ........... A61B 2018/00184; A61B 2018/00196; A61B 2018/0091; A61B 2018/00922;
(Continued)

(56) References Cited

U.S. PATENT DOCUMENTS 4,545,375 A * 10/1985 Cline ................. A61B 18/1402
200/302.2
4,562,838 A 1/1986 Walker
(Continued)

FOREIGN PATENT DOCUMENTS

WO 9205743 A1 4/1992
WO 0028908 A1 5/2000
(Continued)

OTHER PUBLICATIONS

Supplementary European Search Report dated Feb. 13, 2017 in connection with EP14845743.
(Continued)

*Primary Examiner* — Ronald Hupczey, Jr.
*Assistant Examiner* — Bradford C. Blaise
(74) *Attorney, Agent, or Firm* — Carter, DeLuca & Farrell LLP

(57) ABSTRACT

An electrosurgical tool or pencil for use in performing surgery includes an elongate, non-conductive housing having an elongate passage extending from a front end. An elongate electrode is mounted in the passage and slidable therein and has an operating forward section, an insulated central section, and an non-insulated rear section. The electrode can be adjusted in its longitudinal direction by a user. A conducting member is mounted on the rear section of the electrode and an elongate conducting strip is fixedly mounted in the elongate passage adjacent one side of the electrode and parallel thereto. The strip is supported by the housing so as to be in electrical contact with the conducting member which is slidable relative to the conducting strip. A circuit board for controlling the tool's operation is mounted in the housing and connected to the conducting strip.

7 Claims, 7 Drawing Sheets

(52) U.S. Cl.
CPC ............ *A61B 2018/00184* (2013.01); *A61B 2018/00196* (2013.01); *A61B 2018/00595* (2013.01); *A61B 2018/00601* (2013.01); *A61B 2018/00922* (2013.01); *A61B 2018/1475* (2013.01)

(58) Field of Classification Search
CPC .. A61B 2018/00946; A61B 2018/1475; A61B 2018/00589; A61B 2018/00595; A61B 2018/00601; A61B 18/14; A61B 18/1402; A61B 18/1477
See application file for complete search history.

(56) References Cited

U.S. PATENT DOCUMENTS

| | | | |
|---|---|---|---|
| 4,625,723 A | 12/1986 | Altnether et al. |
| 4,683,884 A | 8/1987 | Hatfield et al. |
| 4,719,914 A | 1/1988 | Johnson |
| 4,850,352 A | 7/1989 | Johnson |
| 4,911,159 A | 3/1990 | Johnson et al. |
| 4,919,129 A | 4/1990 | Weber, Jr. et al. |
| 5,013,300 A | 5/1991 | Williams |
| 5,035,695 A | 7/1991 | Weber, Jr. et al. |
| 5,071,418 A | 12/1991 | Rosenbaum |
| 5,085,657 A | 2/1992 | Ben-Simhon |
| 5,108,389 A | 4/1992 | Cosmescu |
| 5,154,709 A | 10/1992 | Johnson |
| 5,181,916 A | 1/1993 | Reynolds et al. |
| 5,192,267 A | 3/1993 | Shapira et al. |
| 5,197,963 A | 3/1993 | Parins |
| 5,199,944 A | 4/1993 | Cosmescu |
| 5,226,904 A | 7/1993 | Gentelia et al. |
| 5,234,428 A | 8/1993 | Kaufman |
| 5,242,442 A | 9/1993 | Hirschfeld |
| 5,318,516 A | 6/1994 | Cosmescu |
| 5,318,565 A | 6/1994 | Kuriloff et al. |
| 5,348,555 A | 9/1994 | Zinnanti |
| 5,360,427 A | 11/1994 | Majlessi |
| 5,376,089 A | 12/1994 | Smith |
| 5,413,575 A | 5/1995 | Haenggi |
| 5,431,650 A | 7/1995 | Cosmescu |
| 5,449,357 A | 9/1995 | Zinnanti |
| 5,451,222 A | 9/1995 | De Maagd et al. |
| 5,451,223 A | 9/1995 | Ben-Simhon |
| 5,460,602 A | 10/1995 | Shapira |
| 5,479,019 A | 12/1995 | Gross |
| 5,496,314 A | 3/1996 | Eggers |
| D373,190 S | 8/1996 | Monson |
| 5,554,172 A | 9/1996 | Horner et al. |
| 5,578,000 A | 11/1996 | Greff et al. |
| 5,593,406 A | 1/1997 | Eggers et al. |
| 5,609,573 A | 3/1997 | Sandock |
| 5,626,577 A | 5/1997 | Harris |
| D384,148 S | 9/1997 | Monson |
| 5,674,219 A | 10/1997 | Monson et al. |
| 5,681,262 A | 10/1997 | Isse |
| 5,693,044 A | 12/1997 | Cosmescu |
| 5,707,402 A | 1/1998 | Heim |
| 5,797,901 A | 8/1998 | Cosmescu |
| 5,800,431 A | 9/1998 | Brown |
| 5,830,214 A | 11/1998 | Flom et al. |
| 5,836,909 A | 11/1998 | Cosmescu |
| 5,836,944 A | 11/1998 | Cosmescu |
| 5,935,125 A | 6/1999 | Zupkas |
| 5,951,548 A | 9/1999 | DeSisto et al. |
| 5,968,042 A | 10/1999 | Ernster |
| 6,099,525 A | 8/2000 | Cosmescu |
| 6,120,498 A | 9/2000 | Jani et al. |
| 6,142,995 A | 11/2000 | Cosmescu |
| 6,149,648 A | 11/2000 | Cosmescu |
| 6,197,024 B1 | 3/2001 | Sullivan |
| 6,258,088 B1 | 7/2001 | Tzonev et al. |
| 6,287,305 B1 | 9/2001 | Heim et al. |
| 6,355,034 B2 | 3/2002 | Cosmescu |
| 6,364,853 B1 | 4/2002 | French et al. |
| 6,451,017 B1 | 9/2002 | Moutafis et al. |
| 6,458,125 B1 | 10/2002 | Cosmescu |
| 6,524,307 B1 | 2/2003 | Palmerton et al. |
| 6,533,781 B2 | 3/2003 | Heim et al. |
| 6,558,379 B1 | 5/2003 | Batchelor et al. |
| 6,602,249 B1 | 8/2003 | Stoddard et al. |
| 6,616,658 B2 | 9/2003 | Ineson |
| 6,635,034 B1 | 10/2003 | Cosmescu |
| 6,702,812 B2 | 3/2004 | Cosmescu |
| 6,899,712 B2 | 5/2005 | Moutafis et al. |
| 6,918,902 B2 | 7/2005 | French et al. |
| 7,033,353 B2 | 4/2006 | Stoddard et al. |
| 7,083,601 B1 | 8/2006 | Cosmescu |
| 7,112,199 B2 | 9/2006 | Cosmescu |
| 7,172,592 B2 | 2/2007 | DeSisto |
| 7,303,559 B2 | 12/2007 | Peng et al. |
| 7,329,253 B2 | 2/2008 | Brounstein et al. |
| 7,377,919 B2 | 5/2008 | Heim et al. |
| 7,731,713 B2 | 6/2010 | Christoudias |
| 7,761,188 B2 | 7/2010 | Palmerton et al. |
| 7,828,794 B2 | 11/2010 | Sartor |
| 7,935,109 B2 | 5/2011 | Cosmescu |
| 7,967,816 B2 | 6/2011 | Ocel et al. |
| 8,022,327 B2 | 9/2011 | Blomeyer |
| 8,057,470 B2 | 11/2011 | Lee et al. |
| 8,095,241 B2 | 1/2012 | Palmerton et al. |
| 8,109,929 B2 | 2/2012 | Eitenmueller |
| 8,211,103 B2 | 7/2012 | Greep |
| 8,319,134 B2 | 11/2012 | Blomeyer |
| 8,414,576 B2 | 4/2013 | Cosmescu |
| 8,518,018 B2 | 8/2013 | Minskoff et al. |
| 8,690,872 B2 | 4/2014 | Jayaraj |
| 8,702,700 B2 | 4/2014 | Maeda et al. |
| 2002/0019631 A1 | 2/2002 | Kidder et al. |
| 2002/0058931 A1 | 5/2002 | Parker et al. |
| 2002/0103485 A1 | 8/2002 | Melnyk et al. |
| 2003/0088247 A1 | 5/2003 | Ineson |
| 2004/0092927 A1 | 5/2004 | Podhajsky et al. |
| 2004/0267326 A1 | 12/2004 | Ocel et al. |
| 2006/0058778 A1 | 3/2006 | Arcusa Villacampa et al. |
| 2006/0264928 A1 | 11/2006 | Kornerup et al. |
| 2007/0066970 A1 | 3/2007 | Ineson |
| 2007/0129722 A1 | 6/2007 | Cosmescu |
| 2007/0249990 A1 | 10/2007 | Cosmescu |
| 2007/0260239 A1 | 11/2007 | Podhajsky et al. |
| 2008/0103431 A1 | 5/2008 | Brounstein et al. |
| 2008/0319455 A1* | 12/2008 | Harris ............... A61B 17/0684 606/139 |
| 2010/0094283 A1 | 4/2010 | Cosmescu |
| 2010/0113942 A1* | 5/2010 | Eberle ............... A61B 1/00165 600/478 |
| 2010/0125172 A1 | 5/2010 | Jayaraj |
| 2011/0034921 A1 | 2/2011 | Sartor |
| 2011/0077645 A1 | 3/2011 | Lin |
| 2011/0190768 A1 | 8/2011 | Shvetsov et al. |
| 2011/0230878 A1 | 9/2011 | Ryan et al. |
| 2011/0319892 A1 | 12/2011 | Blomeyer |
| 2012/0203223 A1 | 8/2012 | Terry et al. |
| 2012/0283718 A1 | 11/2012 | Cosmescu |
| 2012/0283728 A1 | 11/2012 | Cosmescu |
| 2013/0006236 A1 | 1/2013 | Greep et al. |
| 2013/0204246 A1 | 8/2013 | Greep et al. |
| 2014/0081086 A1 | 3/2014 | Shvetsov et al. |

FOREIGN PATENT DOCUMENTS

| | | |
|---|---|---|
| WO | 2012155922 A2 | 11/2012 |
| WO | 2013121226 A1 | 8/2013 |
| WO | 2014/032157 A1 | 3/2014 |
| WO | 2015039232 A1 | 3/2015 |

OTHER PUBLICATIONS

Chinese Office Action dated Dec. 15, 2017 issued in corresponding Chinese Appln. No. 201480051435.7.
Japanese Office Action dated Jun. 25, 2018 issued in corresponding Japanese Appln. No. 2016-543274.

(56) References Cited

OTHER PUBLICATIONS

International Search Report for PCT/CA2014/050876 dated Dec. 19, 2014.
Australian Examination Report issued in Appl. No. AU 2014324006 dated May 23, 2018 (3 pages).
Japanese Notice of Allowance dated Oct. 17, 2018 issued in corresponding JP Appln. No. 2016-543274. (Summary only).

* cited by examiner

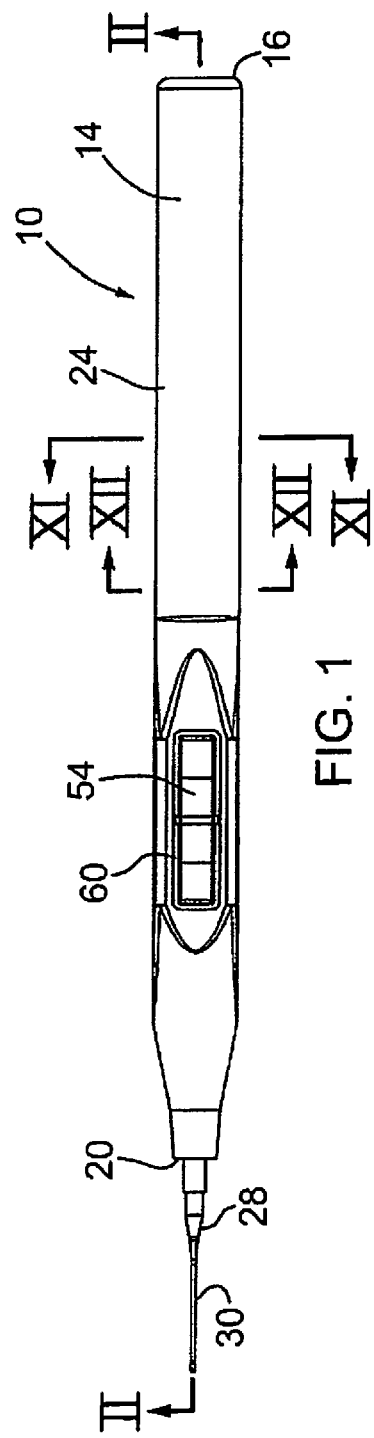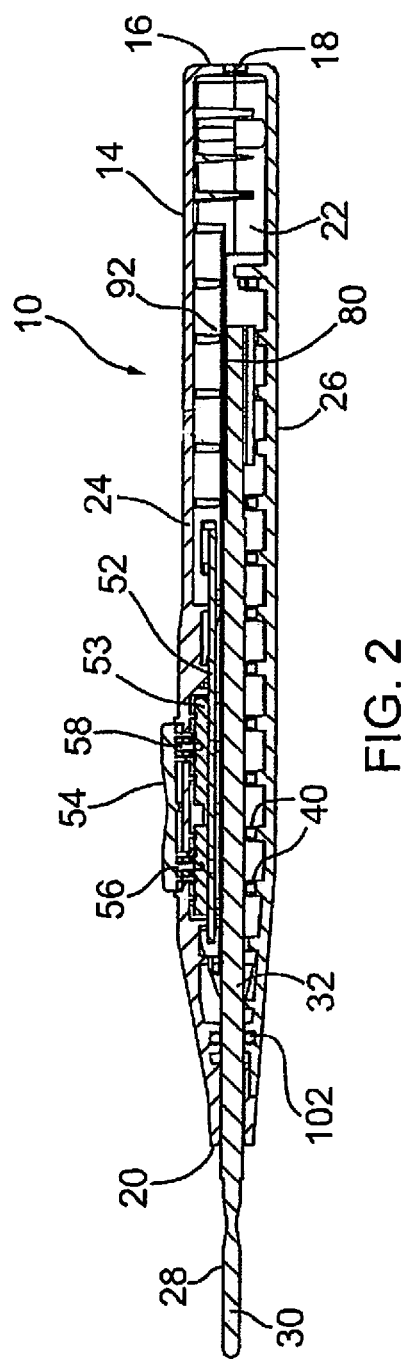

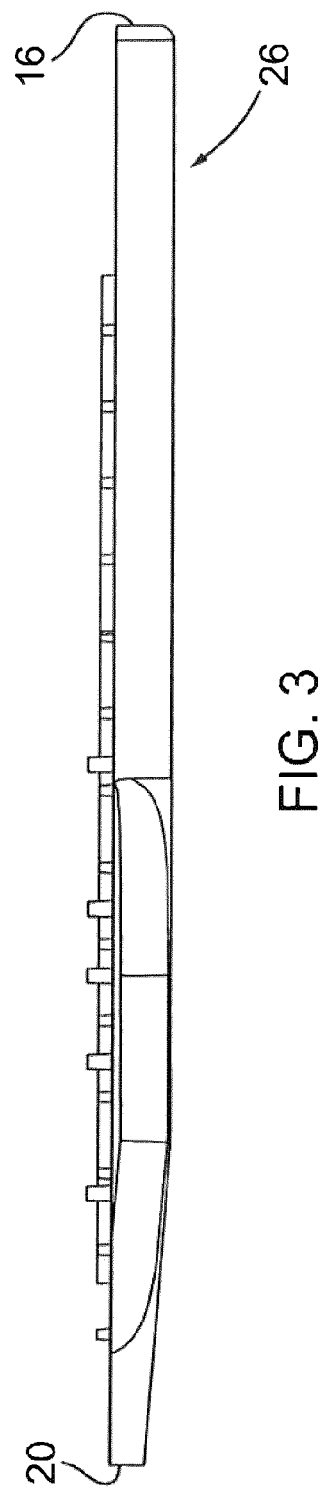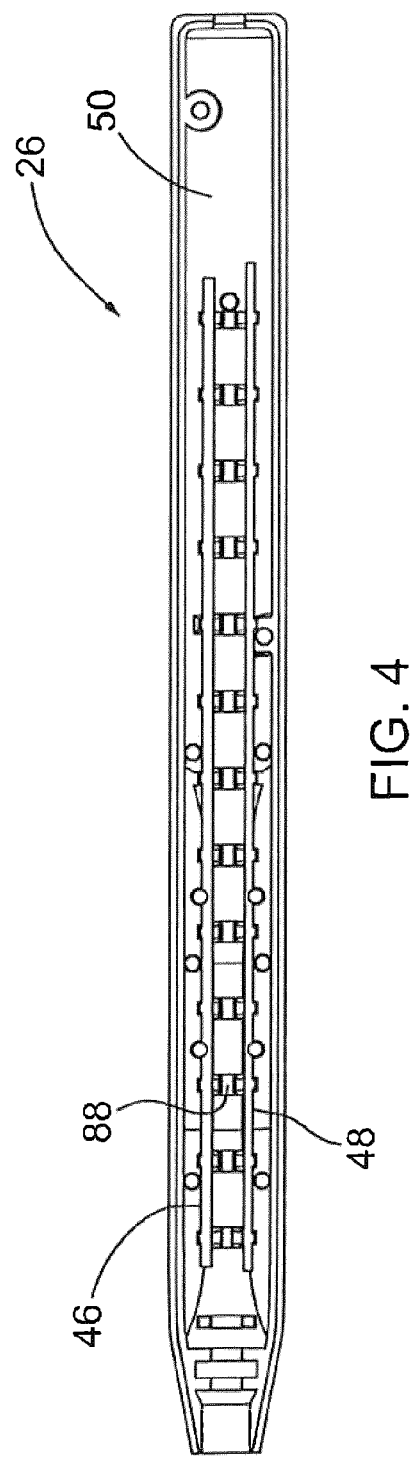

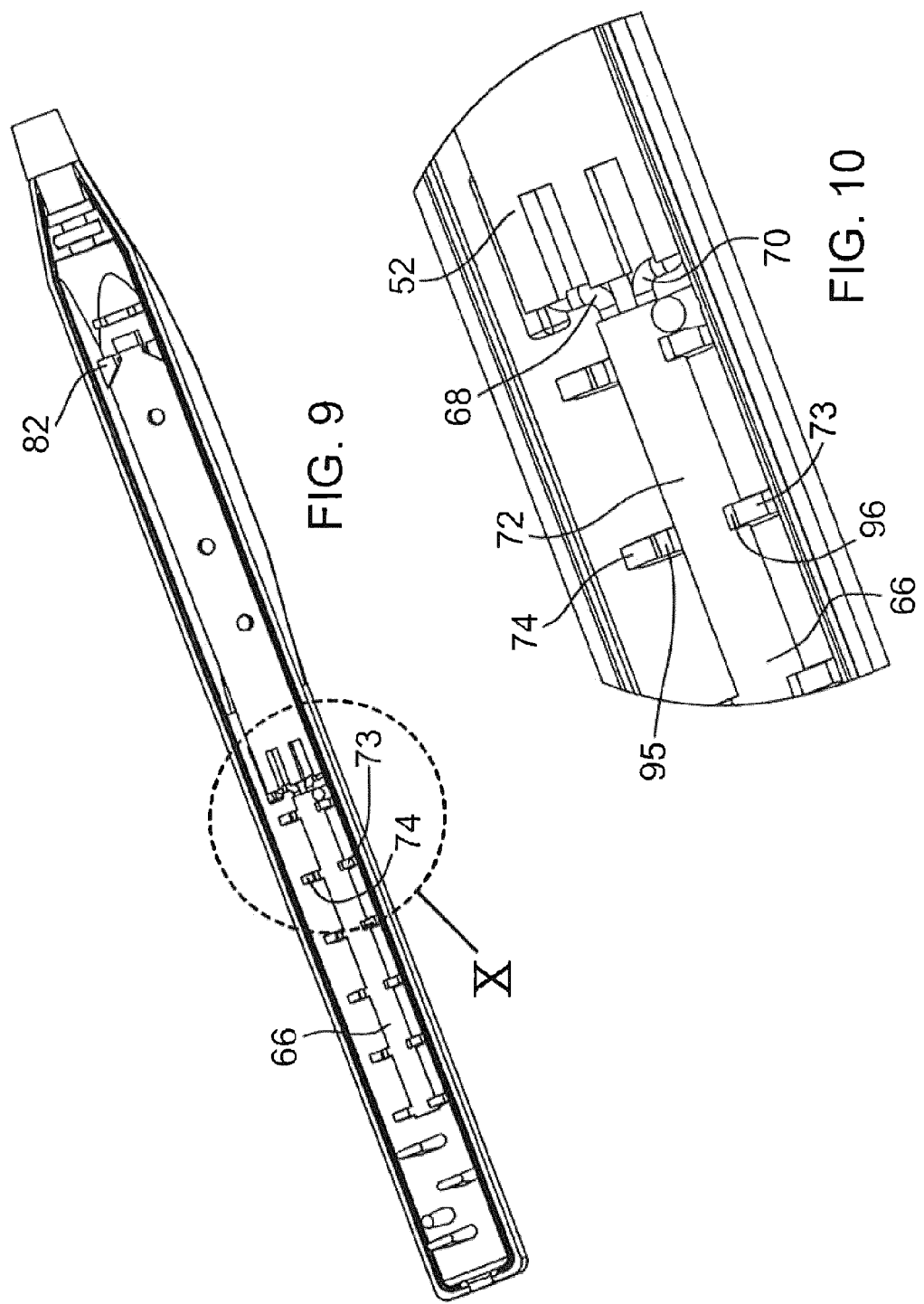

ADJUSTABLE ELECTROSURGICAL PENCIL

CROSS-REFERENCE TO RELATED APPLICATIONS

The present application is a U.S. National Stage application under 35 U.S.C. § 371(a) of PCT/CA2014/050876 filed on Sep. 15, 2014, which claims priority to and the benefit of, Canadian Application Serial No. 2827695, filed on Sep. 20, 2013, the entire contents of all which are incorporated by reference herein.

BACKGROUND

This disclosure relates to electrosurgical tools for use in performing surgery on a surgical site and, in particular, relates to electrosurgical pencils which can be held in one hand by a surgeon and which can be connected to a suitable power source.

Electrosurgery can be used for cutting tissue, coagulating bleeding or achieving a combination thereof using electrical energy which can be provided by an electrosurgical generator. Energy for the operation is applied to the tissue through a blade electrode held in a hand piece by a surgeon. To apply the energy, the electrosurgical (ESU) pencil is activated by the surgeon by pressing a switch which can be located on the hand piece. If a single finger switch is used, the switch may have one position for providing a certain level of energy to achieve cutting while a different position of the switch supplies a different energy waveform to achieve coagulation. The electrosurgical pencil can be constructed as a disposable unit that is only used for one operation.

Published US application no. 2007/0260239 to R. J. Podhajsky et al. describes an electrosurgical pencil having a variable control. The pencil includes an elongate housing with an electrocautery blade supported within the housing and extending distally from its front end. This pencil has an activation button supported on the housing. The housing has a blade receptacle located at its front end which can receive the replaceable blade. The pencil is coupled to a conventional generator via a cable attached to the rear end of the pencil.

U.S. Pat. No. 5,626,577 issued May 6, 1977 to G. A. Harris describes an ESU tool or pencil which has a non-conductive main housing on which is at least one actuating button to selectively control the electrical current from an attached cord. The housing forms in the elongate aperture or passage extending from an open front end. An electrode housing is mounted in the main housing and it closely receives a relatively short electrode which is said to be either disposable or reusable. An electrically conductive material surrounds the internal passage of the electrode housing to provide an electrical connection for the electrode. There is also an elongate conductive post extending down the center of the main housing and received within the post end of the electrode housing which is covered with a non-conductive insulating sleeve. The electrode housing can slide upon the conductive post to allow adjustment to the position of the electrode housing in relation to the main housing.

Published US application no. 2003/0088247 dated May 8, 2003 describes an ESU pencil with the main body portion forming a handle and a wire retaining passage defined in the main body portion. In the front end of the main body is an electrode-receiving opening in which an electrode tip is mounted. Use of the electrode is controlled by a single-pole double-throw rocker type electrical switch mounted on top of the housing and mounted on a small circuit board. An insulated wire enters the wire-retaining passage of the housing through a rear opening and is connected to one terminal of the switch.

There is a need for an improved electrosurgical tool for use in performing surgery, which can be made at a reasonable cost so that the tool can be disposable and which also allows the elongate electrode to be adjusted in its longitudinal direction so that it can be moved from a retracted position to any one of a number of extended positions during the course of a surgical operation.

SUMMARY

According to one embodiment of the present disclosure, an electrosurgical tool for use in performing surgery on a surgical site includes an elongate, non-conductive housing having a rear end, a front end, an elongate passage extending into the housing from the front end. An elongate electrode for performing electrosurgery is mounted in the elongate passage and slidable therein. The electrode has an operating forward section projecting from the housing, an insulating central section, and a non-insulated rear section and the position of the electrode is adjustable in its longitudinal direction by a user between a retracted position and a selected one of a plurality of extended positions. An electrically conducting member is mounted on the rear section of the electrode and is slidable therewith. An elongate conducting strip is fixedly mounted in the elongate passage adjacent one side of the electrode and parallel thereto. This strip is supported by the housing so as to be in electrical contact with the electrically conducting member, which is slidable relative to the conducting strip. The tool further includes an electrical circuit board for controlling electrical operation of the electrode, this circuit board being mounted in the housing, connected to the conducting strip and connectable to a power source. During use of the tool, the circuit board can provide electrical current through the conducting strip to the electrode in the retracted position and in any one of the extended positions of the electrode.

In an exemplary version of this tool, the electrically conducting member is a split metal sleeve detachably mounted on the electrode by means of a friction fit.

According to another embodiment of the present electrosurgical tool for use in performing surgery, the tool includes an elongate housing have a rear end, a front end, and an elongate passage extending through the housing from an opening in the front end and towards the rear end. An elongate electrode for performing electrosurgery has a length of at least 10 cm and is slidably mounted in the passage. The electrode has an non-insulated forward section projecting from the front end of the housing and an insulated major section extending rearwards from the forward section. An electrical circuit board is provided to control electrical operation of the electrode and is mounted on side of the electrode in the housing. The circuit board has an insulated wire connected thereto for providing electrical power to the circuit board. An elongate conductor is fixedly attached to a bottom of the circuit board and extends along one side of the electrode and parallel thereto. This conductor extends rearwardly from the circuit board and is electrically insulated from an exterior surface of the housing. During use of the tool, the circuit board can provide electrical power through the elongate conductor to the electrode both when the electrode is retracted into the housing and when the electrode is in any one of a plurality of possible extended positions.

According to an exemplary version of this tool, the elongate housing is made from top and bottom half sections molded of plastic material and welded together. The bottom half section is formed internally with a series of space-apart transverse ribs formed with central, electrode-receiving grooves. The electrode is mounted in these grooves and slidable therein in the longitudinal direction of the housing.

According to a further aspect of the present disclosure, a method is provided for manufacturing an electrosurgical pencil for use in performing surgery. This method comprises providing top and bottom half sections for assembly of a plastic pencil housing having front and rear ends and an elongate passage extending lengthwise from the front end. Also an electrical circuit board is provided for controlling electrical operation of the pencil and an elongate conducting strip is fixedly connected to a bottom of the circuit board so as it would extend from at least one end of the circuit board. An elongate electrode for performing electrosurgery is mounted in one of the two half sections for sliding movement relative to the one half section. The elongate electrode has an operating forward section, an insulated central section, and an non-insulated rear section. The top half section is mounted on the bottom half section so that the circuit board is located in the top half section and the conducting strip extends along and is next to one side of the electrode. The constructing strip is in electrical contact with the rear section of the electrode. Then the top and bottom half sections are permanently bonded together to form the housing and the passage which is open at its front end so that the electrode projects out of the passage.

In an exemplary version of this method, the circuit board has an insulated power wire connected to a rear end thereof and this power wire extends through a rear opening formed in a rear end of the half sections.

Further features and advantages of the electrosurgical tool or pencil of the present disclosure will become apparent from the following detailed description taken in conjunction with the accompanying drawings.

BRIEF DESCRIPTION OF THE DRAWINGS

FIG. 1 is a top view of an electrosurgical (ESU) pencil constructed in accordance with the disclosure;

FIG. 2 is a longitudinal cross-section of the pencil, this cross-section being taken along the line II-II of FIG. 1;

FIG. 3 is a longitudinal side view of a lower half section of the housing for the pencil of FIG. 1;

FIG. 4 is a top view of the lower half of the housing shown in FIG. 3;

FIG. 9 is a bottom view of the upper portion of the pencil housing, this view showing the circuit board arranged therein;

FIG. 10 is a detail view of the encircled area X indicated in FIG. 9, this view showing one end of a power supply line connected to the circuit board;

DETAILED DESCRIPTION

Figure 6:
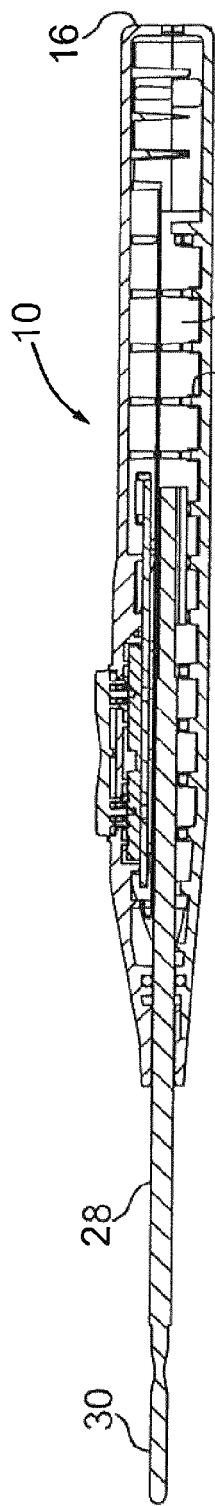
FIG. 6 is a longitudinal cross-section similar to FIG. 2 but showing the electrode in an extended position.

FIGS. 1, 2 and 6 illustrate an exemplary embodiment of an electrosurgical tool 10, often referred to as an electrosurgical pencil, constructed in accordance with the disclosure. The ESU pencil 10 is for use in performing surgery on a surgical site. The pencil includes an elongate, non-conductive housing or main body 14 forming a handle gripable by a trained user, for example a surgeon. The housing is shaped for ease of comfort by the user and has a rear end 16, which can have a central hole 18 formed therein, a front end 20, and an elongate passage 22 extending into the housing from the front end. The housing is made from a suitable plastic material such as polyethylene and, in the exemplary version shown, is made from two half sections including top half section 24 and bottom half section 26. These sections extend the length of the housing and can be rigidly and permanently attached to each other by such known methods as ultrasonic welding or adhesive bonding. It should be understood that the exemplary illustrated pencil 10 is intended for one time use only and is disposed of after surgery.

Figure 5:
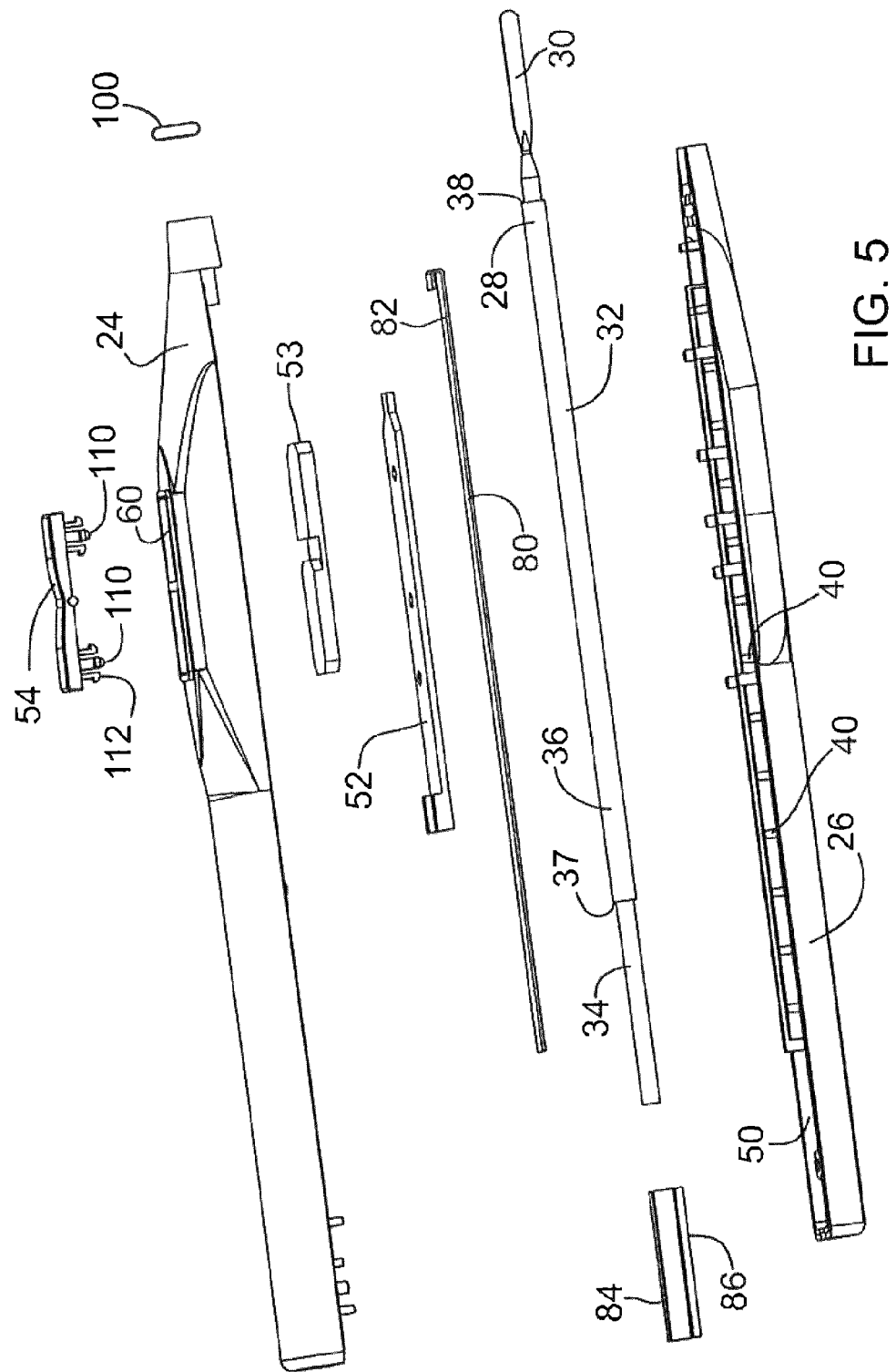
FIG. 5 is an exploded view of the principal components that make up the ESU pencil of FIG. 1.
Figure 7:
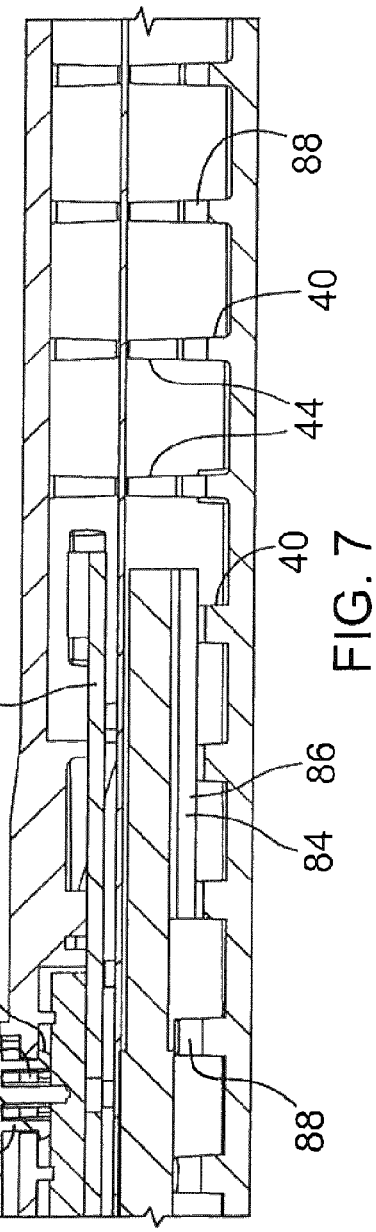
FIG. 7 is a cross-sectional detail taken along the line II-II of FIG. 1 but showing a central section of the ESU pencil.
Figure 8:
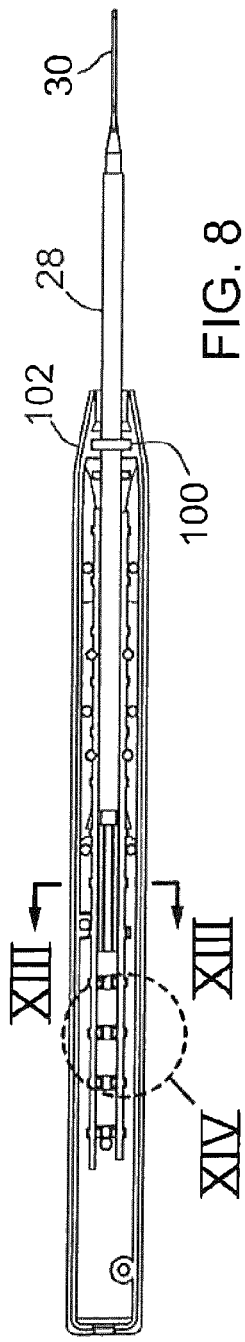
FIG. 8 is a plan view of the bottom portion of the pencil housing similar to FIG. 4 but showing an elongate electrode mounted in this lower portion.

The bottom half section 26 is shown separately in FIGS. 3 and 4 and also in FIG. 8 wherein an elongate electrode to perform electrosurgery is shown mounted in the half section. The exemplary illustrated electrode 28 is mounted in the elongate passage 22 and slidable therein and thus the longitudinal position of the electrode is adjustable by the surgeon by pulling or pushing on the exposed end. The illustrated electrode has an operating forward section 30 projecting from the housing, an insulated central section 32 and a non-insulated rear section 34. The central section 32 can be covered in a layer of insulating plastic in a manner known per se, this plastic being indicated at 36 in FIG. 5 and extending from a rear end at 37 to a forward end 38. As indicated, the position of the electrode is adjustable in its longitudinal direction by a user between a retracted position which can be defined by a suitable stop provided within the housing and a selected one of a plurality of extended positions. An extended position of the electrode is shown in both FIGS. 6 and 8. As shown, the forward section 30 of the electrode can be formed as a flattened blade. Normally the plane of the blade is vertical if the pencil itself is in the upright position shown in FIGS. 2 and 6. The exemplary illustrated housing 14 is formed with integral transverse ribs 40 in the bottom half section. These transverse ribs are shown in cross section in FIG. 7. In order to accommodate and slidably receive the electrode 28, the transverse ribs 40 are formed with central electrode-receiving grooves 44. Also extending in the longitudinal direction along the bottom half section of the housing are two internal guide walls 46, 48 located on opposite sides of the grooves 44. The rear ends of these walls are spaced from the rear end of the housing to leave an open area 50 visible in FIGS. 4 and 5.

The ESU pencil includes an electrical circuit board 52 for controlling electrical operation of the electrode 28. An electrical switch mechanism 54 is mounted on the main body portion for housing 14 so as to be operable externally on the pencil and the circuit board is operated by this switch mechanism and an electrical push button device mounted on the circuit board. The switch 54 can be a rocker switch similar to that used in applicant's U.S. Pat. No. 6,616,658. The switch 54 is a single poll, double throw rocker type electrical switch mounted on top of the housing and above the circuit board. The illustrated switch has two downwardly projecting pins 56, 58 which projects through two holes in a recessed section 60 of the housing, this section shown in FIG. 5. Two round holes, one of which is visible at 62 in FIG. 7 are formed near opposite ends of the recessed section. In use the forward end of the switch can be pressed by the surgeon to provide a higher frequency signal to the electrode for cutting tissue and the rearward end of the switch is pressed to provide a lower frequency signal to the electrode for cauterizing tissue. If desired, the switch could be a simple on-off switch if the electrode is intended to operate in only one mode.

As illustrated in FIGS. 9 and 10, an insulated power line or wire 66 is provided in the rear section of the housing to provide electrical power to the circuit board. This line extends through the opening 18 at the rear end of the housing and connects to the rear end of the circuit board as illustrated in FIG. 10 which shows two small wires 68, 70 attached to the circuit board. The two wires extend through an insulating sheath 72 and although only partially shown in the figures, the combined wire 66 including the insulating sheath extends rearward to the rear end of the housing and out of the housing to the power source. The wire 66 is held in place in the top half section 24 by being gripped between pairs of downward projections 73, 74. There are a series of these pairs of downward projections 73, 74 formed in the top half section and evenly spaced apart as indicated in FIGS. 9 and 10.

Figure 11:
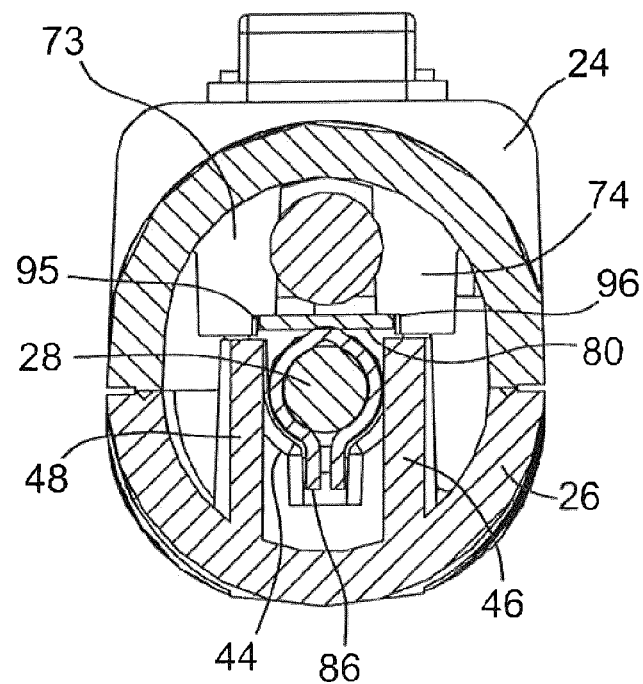
FIG. 11 is a transverse cross-section of the ESU pencil taken along the line XI-XI of FIG. 1.
Figure 12:
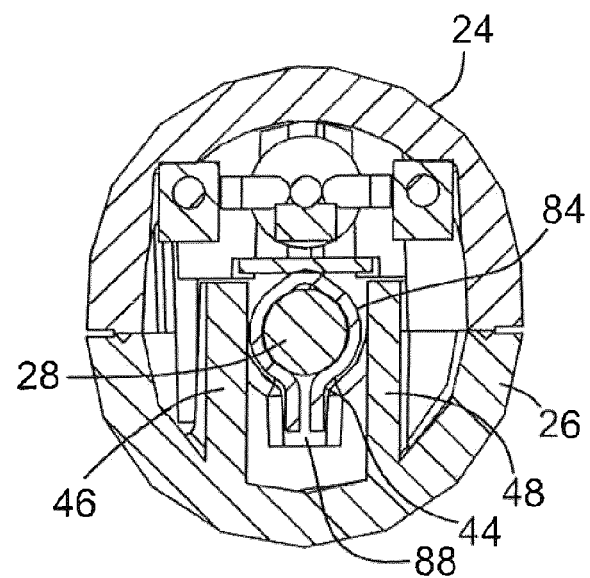
FIG. 12 is another transverse cross-section of the ESU pencil taken along the line XII-XII of FIG. 1.
Figure 13:
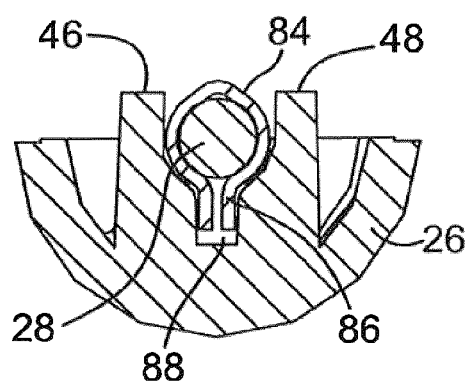
FIG. 13 is a cross-sectional detail of the lower portion of the pencil housing taken along the line XIII-XIII of FIG. 8.

In order to provide power to the electrode 28 from the circuit board, an elongate conducting strip 80 is connected to the bottom of the circuit board. This strip, which is shown separately in FIG. 5, in an exemplary version of the ESU pencil is welded or soldered to the bottom of the circuit board adjacent one end of the strip. The location of the weld or connection as indicated at 82 in FIGS. 5 and 9. The strip 80 is fixedly mounted in the elongate passage 22 of the housing, is adjacent one side of the electrode 28 and is parallel thereto. Further the strip is supported by the pencil housing so as to be in electrical contact with an electrically conducting member 84 mounted on a rear section of the electrode. In an exemplary embodiment of this conducting member, it is a split metal sleeve detachably mounted on the electrode by means of a friction fit. The transverse cross-section of the exemplary conducting member is shown in FIGS. 11 to 13. The conducting member has a least one longitudinal flange 86 formed along one exterior side thereof. However the illustrated exemplary version of the conducting member has two longitudinal flanges 86 extending parallel to one another and closely spaced from each other. The aforementioned transverse ribs 40 in the bottom half section of the housing are respectively formed with slots 88 sized and adapted to receive the longitudinal flanges 86 and thereby prevent rotation of the electrically conducting member 84 and the electrode about their longitudinal axes.

Figure 14:
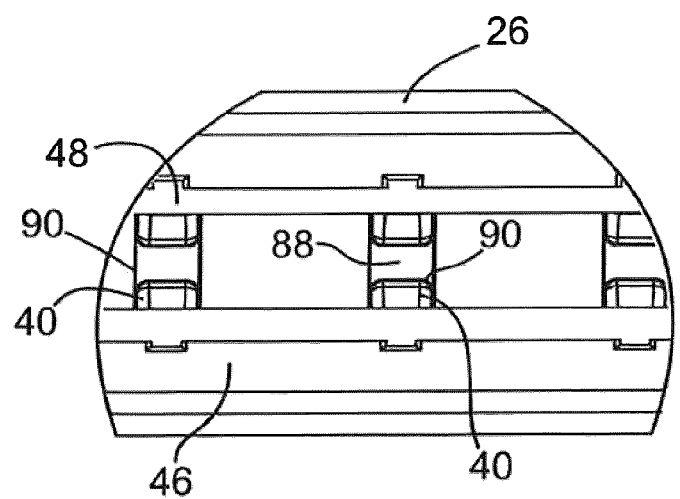
FIG. 14 is a detail view of the circled area XIV of FIG. 8.

In the exemplary housing, the transverse ribs 40 at least in the regions of the series of slots 88 are formed with rounded or chamfered edges to facilitate sliding movement of the electrode 28 in the elongate passage. These chamfered edges are indicated at 90 in FIG. 14 and they help to prevent either end of the conducting member 84 from catching on edges of the ribs 40.

An exemplary form of mounting for the conducting strip 80 will now be described with particular reference to FIGS. 2 and 11. As shown in FIG. 2, the conducting strip 80 extends from a front end of the circuit board to a point 92 rearwards of the rear end of the circuit board and it will understood that it is electrically insulated from an exterior surface of the housing by the insulating plastic material of the housing. The conducting strip is supported to the rear of the circuit board either by the top side of the electrode itself or, at the rear end, by the conducting member 84. When the electrode 28 has been moved forward to an extended position, a rear section of the conducting strip 80 will be supported or prevented from downward movement by the tops of the guide walls 46, 48 formed in the bottom half section 26. It will also be seen from FIG. 11 that the conducting strip 80 is also supported along its longitudinal edges and from above by the downward projections 73, 74 of the top half section. In the exemplary version of the top half section, the projections are formed respectively with notches 95, 96 in their bottom ends, these notches receiving the longitudinal edges of the conducting strip. Thus any sideways movement of the conducting strip is prevented and the conducting strip is supported at its edges from above.

An exemplary form of the ESU pencil 10 is provided with a mechanism for preventing undue or unwanted movement of the electrode 28 in the passage 22. In the exemplary illustrated ESU pencil 10, one or two rubber or rubberlike friction rings 100 are mounted in the housing 14. The ring or rings can take the form of an O ring or rings of suitable size, one of which is shown separately in FIG. 5. A suitable chamber 102 can be formed in the housing 14 adjacent its front end 20. The bottom half of this chamber 102 can be seen in FIG. 8. In order to accommodate possibly two friction rings in the front end of the housing, two of the chambers 102 can optionally be formed in the front end section of the housing. It will be understood that the friction ring or rings extend snugly around the electrode and act to hold the electrode in a selected position in absence of sufficient force being applied to the electrode to move the electrode in its lengthwise direction. The friction created by the ring or rings still allows the surgeon to change the position of the electrode with his or her hand by overcoming the friction force.

Not only is it desirable that the electrode maintain the selected position in the lengthwise direction but it is also desirable that the blade end of the electrode maintain its orientation. When the forward section 30 of the electrode is flat (as shown by FIGS. 1 and 2), most surgeons will select the blade orientation shown, that is with the plane of the flat blade extending vertically with the housing arranged in the upright position. This upright position will generally be maintained by the engagement between the flanges 86 formed on the conducting member 84 and the sides of the slots 88. However in an exemplary version of the pencil, it is possible for the surgeon to change the orientation of the flat blade by manually turning the electrode about its axis, thereby overcoming the friction force between the rear end section of the blade and the conducting member 84.

The disposable ESU pencil 10 described above can be assembled and manufactured at a reasonable cost and in a manner which will provide for reliable, easy operation. The top and bottom half sections 24, 26 can be molded from a suitable insulating plastics material and in a manner which will enable the two half sections to be assembled together to form the complete pencil housing with a front end 20 and a rear end 16. The assembled half sections provide an elongate passage that ends lengthwise from the front end. The electric circuit board which per se can be of known construction in regards to its electronic circuitry is provided for controlling the electrical operation of the pencil 10. The elongate conducting strip 80 is fixedly connected to a bottom of the circuit board so that this strip extends from at least one end of the circuit board, this end being the rear end in the illustrated pencil.

The elongate electrode 28 is mounted in one of the two half sections (prior to assembly of these sections) for sliding movement relative to this one half section. As indicated above, in the illustrated pencil the electrode is mounted in the bottom half section 26. When it is mounted in the half section, its forward section 30 projects from the front end of the half section as shown, for example in FIGS. 1 and 2. In this arrangement, with the electrode mounted in the bottom half section, the circuit board 52 can be mounted in the top half section 24 together with the conducting strip 80 which has been rigidly attached to the bottom of the circuit board. As the two half sections are joined together, the conducting strip is placed along and next to one side of the electrode 28 so that it is in electrical contact with the rear section of the electrode. At the same time, a power wire connected to the rear end of the circuit board is routed through the rear portion of the housing and out through the rear hole 18. With the internal components in place, the top and bottom half sections can be permanently bonded together to form the housing 14 and its passage 22 which is open at the front end of the housing. During this bonding step, the front end section of the electrode projects out of the passage 22.

After the housing has been completed in this manner, the rocker switch 54 for operating the circuit board is mounted on the top half section of the housing. For attachment purposes for, flexible and resilient clips are arranged about the two pins 56, 58. Each of the clips is formed with an outwardly extending end flange 112. The four flanges engage the bottom edge of the circular hole into which the respective pin is pushed as shown in FIG. 7. The bottom end of each pin is able to engage a standard electrical push bottom (not shown) mounted on the top of the circuit board for operation of the board.

While the present disclosure has been illustrated and described as embodied in an exemplary embodiment, e.g. an embodiment having particular utility in surgical applications, it is to be understood that this present disclosure is not limited to the details shown herein, since it will be understood that various omissions, modifications, substitutions and changes in the forms and details of the disclosed electrosurgical pencil, its operation, and its method of manufacture may be made by those skilled in the art without departing in any way from the scope of the present disclosure. For example those of ordinary skill in the art will readily adapt the present disclosure for various other applications without departing from the scope of the present disclosure.

The invention claimed is:

1. An electrosurgical tool for use in performing surgery on a surgical site, said electrosurgical tool comprising:
   an elongate, non-conductive housing having a rear end, a front end, and an elongate passage extending into the housing from the front end, said housing having transverse ribs extending into said elongate passage, each of said transverse ribs defining a groove and a slot that are directly and continuously joined with one another;
   an elongate electrode for performing electrosurgery mounted in said elongate passage and slidable therein, said electrode having an operating forward section projecting from said housing, an insulated central section, and a non-insulated rear section, the position of said electrode being adjustable in its longitudinal direction by a user between a retracted position and a selected one of a plurality of extended positions;
   an electrically conducting member mounted on said rear section of the electrode and slidable therewith, said electrically conducting member slidably received in said groove;
   an elongate conducting strip fixedly mounted in said elongate passage adjacent one side of said electrode and parallel thereto, said elongate conducting strip being supported by said housing so as to be in electrical contact with said electrically conducting member, which is slidable relative to said elongate conducting strip; and
   an electrical circuit board for controlling electrical operation of said electrode, said circuit board being mounted in said housing, connected to said elongate conducting strip, and connectable to a power source,
   wherein, during use of said tool, said circuit board is configured to provide electrical current through said elongate conducting strip to said electrode in the retracted position and in any one of said extending positions of said electrode.

2. The electrosurgical tool according to claim 1, wherein said electrically conducting member is a split metal sleeve detachably mounted on said electrode and in a friction fit engagement with said electrode.

3. The electrosurgical tool according to claim 2, wherein said electrical circuit board is welded to said elongate conducting strip and said elongate conducting strip is rigidly held in said elongate passage by spaced-apart projections integrally formed in said housing and engaging top and bottom sides of said elongate conducting strip.

4. The electrosurgical tool according to claim 2, wherein said electrically conducting member has at least one longitudinal flange formed along one exterior side thereof, said slot of at least one of said transverse ribs configured to receive said at least one longitudinal flange and thereby prevent rotation of said electrically conducting member and said electrode about their longitudinal axes.

5. The electrosurgical tool according to claim 4, wherein said transverse ribs are formed with rounded or chamfered edges that define said groove, said edges configured to facilitate sliding movement of said electrode in said elongate passage.

6. The electrosurgical tool according to claim 5, wherein said housing is made of two half sections molded of rigid plastics material and permanently bonded to one another after mounting of said electrode, its electrically conducting member, said elongate conducting strip, and said circuit board inside the half sections.

7. The electrosurgical tool according to claim 6, wherein said circuit board has wire connectors mounted at one end thereof and connected to an insulated electrical line, which extends from the rear end of the housing.

* * * * *